US00PP17969P3

(12) United States Plant Patent
Lemon

(10) Patent No.: US PP17,969 P3
(45) Date of Patent: Aug. 28, 2007

(54) ***GERANIUM* PLANT NAMED 'MAESTRO DEEP LAVENDER'**

(50) Latin Name: *Pelargonium×hortorum*
Varietal Denomination: Maestro Deep Lavender

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 194 days.

(21) Appl. No.: 11/177,082

(22) Filed: Jul. 8, 2005

(65) Prior Publication Data

US 2007/0011793 P1 Jan. 11, 2007

(51) Int. Cl.
*A01H 5/00* (2006.01)

(52) U.S. Cl. ..... Plt./329

(58) Field of Classification Search ..... Plt./329
See application file for complete search history.

*Primary Examiner*—Kent Bell
(74) *Attorney, Agent, or Firm*—The Webb Law Firm

(57) ABSTRACT

'Maestro Deep Lavender' is a new variety of *geranium* having a free flowering, excellent greenhouse and outdoor performance, and deep lavender colored flowers.

1 Drawing Sheet

Botanical classification: *Pelargonium×hortorum.*
Varietal denomination: 'Maestro Deep Lavender'.

BACKGROUND OF THE INVENTION

The present invention comprises a new and distinct cultivar of *Pelargonium×hortorum* known by the varietal name 'Maestro Deep Lavender'. The new variety was discovered in Lompoc, Calif. The new variety is a result of cross breeding 'Tiffany' (female parent) (unpatented) and 'Americana New Violet' (male parent) (unpatented). The purpose of the breeding program was to develop compact zonal geraniums. The new variety exhibits more free flowering when compared to its female parent. 'Maestro Deep Lavender' is free flowering like its male parent, but exhibits double flowers and a different flower color. The new variety also differs in leaf color and the deepness of the lavender colored petals in comparison to 'Tango Lavender'. Free flowering, good leaf zonation, and excellent greenhouse and outdoor performance of 'Maestro Deep Lavender' helps to distinguish it from other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in Connellsville, Pa. using full light, 16° C. night temperature and 20° C. day temperature and grown in a soilless media with constant fertilizer at 200–250 ppm nitrogen and potassium. The new variety exhibits rooting at 7–10 days under optimal conditions and has a response time of six to seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
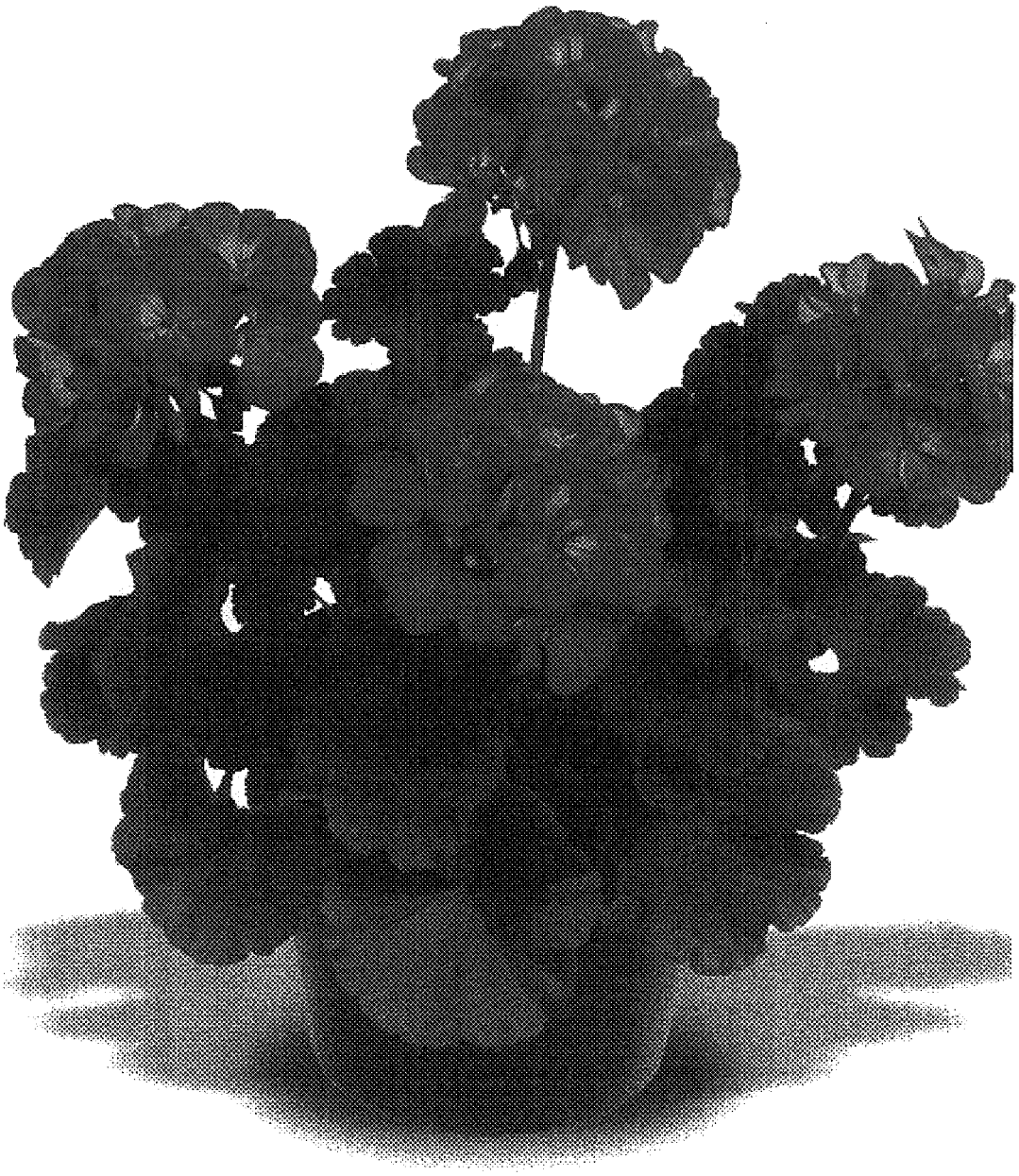

The following detailed description sets forth the characteristics of the new cultivar. The data which defines these characteristics were collected by asexual reproductions carried out in Connellsville, Pa. The new variety was seven weeks old from a rooted cutting when described. The color readings were taken indoors under 200–220 foot candles of cool white fluorescent light. Color references are primarily to the 1966 R.H.S. Colour Chart of The Royal Horticultural Society of London.

PLANT

Market class: Zonal.
Time to initiate roots (days, temperature): About 7–10 days at about 23° C.
Time to develop roots (days, temperature): About 21 days at about 23° C.
Time to produce a finished flowering plant from a rooted cutting: About 6–7 weeks in a 10 cm. container.
Rooting habit: Good; normal.
Form: Round-mounded.
Height from media surface to top of foliage: 12.7–14 cm.
Height from media surface to top of flowers: 25.5–28.7 cm.
Plant diameter: 25.5–28.0 cm.
Vigor: 3 on a scale of 5.
Strength: No artificial support is needed.
Branching habit: Free branching.
Stem:
- *Main stem length.*—7.0–11.0 cm.
- *Diameter.*—0.6–0.8 cm.
- *Color.*—Yellow-Green Group 144B.
- *Texture.*—Fuzzy-leather texture.
- *Pubescence.*—Present.
- *Internode length.*—1.5–1.9 cm.

Lateral branches:
- *Length.*—Primary: 3.6–4.8 cm. Secondary: Plant is too young to measure.
- *Diameter.*—Primary: 0.7–0.8 cm. Secondary: Plant is too young to measure.

*Internode length.*—1.8–2.7 cm.
*Texture.*—Leathery.
*Pubescence.*—Present.
*Color.*—Yellow-Green Group 144B.

Foliage:
*Arrangement.*—Alternate.
*Stipules.*—Size: 0.5–0.8 cm. Color: Yellow-Green Group 144B.
*Zone.*—Location: Very faint zone from outer edge of leaf to ⅔ of the way toward the center. Color: Green Group 137B.
*Size of leaf.*—Length: 8.0–9.9 cm. Width: 9.3–10.9 cm.
*Shape of leaf* (*generally*).—Reniform with a stalked base.
*Shape of apex.*—Rounded in accordance with reniform leaf shape.
*Shape of base.*—Cordate.
*Texture.*—Velvety.
*Aspect.*—Leaves have a slight slope increasing from point of connection toward the margin.
*Margin type.*—Crenate.
*Pubescence.*—Upper surface: Moderate. Lower surface: Moderate.
*Color.*—Young leaves: Upper surface: Green Group 137B. Lower surface: Green Group 138B. Mature leaves: Upper surface: Green Group 137A. Lower surface: Green Group 137C.
*Petiole.*—Length: 4.0–11.0 cm. Diameter: 0.4 cm. Color: Yellow-Green Group 144A.
*Veins.*—Venation type: Palmate. Color: Upper surface: Green Group 138A. Lower surface: Yellow-Green Group 145B.

INFLORESCENCE

Bud:
*Stage of development when bud characteristics determined.*—Bud shows color at side but sepals are not parting at the tips.
*Shape of cluster.*—Elliptical.
*Diameter of cluster.*—1.6–2.8 cm.
*Number of buds per cluster.*—12–25.
*Shape of individual bud.*—Ellipse.
*Length of individual bud.*—1.0–1.3 cm.
*Width of individual bud.*—0.5–0.8 cm.

Natural flowering season at specified location(s): Year round horticultural greenhouse crop.
Blooming habit: Continuous and free flowering.
Umbel diameter: 7.5–8.4 cm.
Umbel depth: 6.7–8.2 cm.
Borne: Umbel, flowers on pedicel, pedicel on peduncle.
Inflorescence position: Above foliage.
Number of inflorescences per lateral branch: 1–2.
Lastingness of an individual flower: 10–14 days.

Florets:
*Form.*—Flat and slightly cupped. As flowers mature, the florets gradually become more open/flat.
*Number per umbel.*—15–21.
*Diameter.*—4.4–4.9 cm.
*Depth.*—1.4–2.4 cm.

Petals:
*Color.*—Upper surface: On each floret the top 2–3 petals have a pronounced white eye whereas the bottom petals do not. The top florets begin as Red-Purple Group 74B on the margin and continue halfway down the petal where there is a faint blotch of Red-Purple Group 72B and then immediately fade to White Group 155D. The venation present is of Red-Purple Group 61B. The bottom florets begin as Red-Purple Group 74B and fade to Red-Purple group 73A toward the bottom third of the petal and then immediately become White Group 155D at the point of connection. The venation present is of Red-Purple Group 61B. Lower surface: Top florets have a Red-Purple Group 74A line on the margin and immediately change to Red-Purple Group 73A. On the bottom ⅓ of the floret there is a White Group 155D blotch that is overshadowed by the Red-Purple Group 67A venation. Bottom florets have a Red-Purple Group 74A line on the margin and immediately change to Red-Purple Group 73A. In the middle of the floret, there is a small White Group 155D blotch. Throughout the floret the venation is Red-Purple Group 67A.
*Shape.*—Inverted teardrop.
*Length.*—2.4–2.9 cm.
*Width.*—1.6–2.1 cm.
*Apex shape.*—Smooth and rounded.
*Base shape.*—Tapered to a point.
*Margin.*—Entire; smooth.
*Number of per floret.*—7–9.
*Texture.*—Smooth.
*Tonality from a distance.*—Deep pink flowers atop of mounding medium-dark green foliage.

Petaloids:
*Quantity.*—0–1 per floret.
*Shape.*—Splits in a two-pronged unit or are tubular.
*Color* (*Upper and lower surface*).—Tubular petals have an upper surface of Red-Purple Group 72A and an inner surface Red-Purple Group 74C and split florets are similar to petals.
*Length.*—0.8–2.4 cm.
*Width.*—0.3–2.1 cm.

Pedicel:
*Length.*—2.2–2.8 cm.
*Diameter.*—0.13–0.15 cm.
*Color.*—Red-Purple Group 60A where the pedicel connects to the floret and fades to Yellow-Green Group 144A as the pedicel approaches the point where it connects to the peduncle. On the bottom half of the pedicel, the upper side takes longer to fade from Red-Purple Group 60A to Yellow-Green Group 144A.

Peduncle:
*Length.*—9.0–13.8 cm.
*Diameter.*—0.3–0.4 cm.
*Texture.*—A slightly rough leather texture with a moderate amount of pubescence. The pubescence becomes longer closer to the point where the peduncle connects to the stem.
*Color.*—Yellow-Green Group 144A.

Sepal:
*Number.*—5.
*Pubescence.*—Moderate.
*Shape.*—Lanceolate.
*Width.*—0.2–0.4 cm.
*Length.*—0.9–1.1 cm.

Fragrance: No unusual fragrance.
Disease resistance: None observed.
Temperature tolerance: None observed.
Drought tolerance: None observed.

REPRODUCTIVE ORGANS

Stamens:
*Number* (*per flower*).—10–13.

*Filament.*—Length: 0.7–0.8 cm. Color: White Group 155D with the tip being Red-Purple Group 66A.

*Anthers.*—Shape: Oval-like with a slight curve. Length: 0.15–0.2 cm. Color: Grey-Purple Group 184C.

*Pollen.*—Color: Greyed-Orange Group 171A. Amount (generally): Plentiful.

Pistils:

*Number.*—1.

*Length.*—0.9 cm.

*Style.*—Length: 0.35 cm. Color: Red-Purple Group 66A.

*Stigma.*—Shape: Style splits and radiates into 5 parts. Color: Red-Purple Group 61A. Size: 0.15 cm. High.

*Ovaries.*—Position: Superior. Pubescence: Present. Length: 0.5 cm. Width: 0.2–0.25 cm. Color: Yellow-Green Group 144B.

I claim:

1. A new and distinct variety of *geranium* plant named 'Maestro Deep Lavender' as herein described and illustrated.

* * * * *